(12) United States Patent
Alani (10) Patent No.: US 6,914,244 B2
(45) Date of Patent: *Jul. 5, 2005

(54) ION BEAM MILLING SYSTEM AND METHOD FOR ELECTRON MICROSCOPY SPECIMEN PREPARATION

(75) Inventor: Reza Alani, Pleasanton, CA (US)

(73) Assignee: Ropintassco Holdings, L.P., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/859,845

(22) Filed: Jun. 3, 2004

(65) Prior Publication Data

US 2004/0217286 A1 Nov. 4, 2004

Related U.S. Application Data

(63) Continuation of application No. 09/874,766, filed on Jun. 5, 2001, now Pat. No. 6,768,110.
(60) Provisional application No. 60/212,963, filed on Jun. 21, 2000.

(51) Int. Cl.$^7$ ............................................... H01L 21/00
(52) U.S. Cl. ...................... 250/307; 250/306; 250/309; 250/492.1; 250/492.2; 250/492.21
(58) Field of Search ............................... 250/306, 307, 250/309, 492.1, 492.2, 492.21

(56) References Cited

U.S. PATENT DOCUMENTS

| | | |
|---|---|---|
| 4,128,765 A | 12/1978 | Franks |
| 4,272,682 A | 6/1981 | Swann |
| 5,009,743 A | 4/1991 | Swann |
| 5,472,566 A | 12/1995 | Swann et al. |
| 5,708,267 A | 1/1998 | Hatakeyama |
| 5,753,924 A | 5/1998 | Swann |
| 5,907,157 A | 5/1999 | Yoshioka et al. |
| 5,922,179 A | 7/1999 | Mitro et al. |
| 5,940,678 A | 8/1999 | Doong et al. |
| 5,986,264 A | 11/1999 | Grunewald |
| 6,194,720 B1 | 2/2001 | Li et al. |
| 6,768,110 B2 * | 7/2004 | Alani .......................... 250/307 |
| 6,784,427 B1 | 8/2004 | Grunewald et al. |

FOREIGN PATENT DOCUMENTS

DE            139 670        1/1980

OTHER PUBLICATIONS

Kawasaki, M. et al., "A new Specimen Preparation Method for Cross–Section TEM Using Diamond Powders" Journal of Electron Microscopy, Japanese Society for Electron Microscopy, Tokyo, JP, vol. 48, No. 2, 1999, pp. 131–137.
Langer, Elektronoenptische Untersuchung des Werkstoffverhaltens in mechanisch belasteten Mikrobauteilen, Dec. 13, 1996, pp. 56–60.

(Continued)

Primary Examiner—John R. Lee
Assistant Examiner—Johnnie L Smith, II
(74) Attorney, Agent, or Firm—Dinsmore & Shohl LLP (57) ABSTRACT

An ion beam milling system and method for electron microscopy specimen preparation is provided and is useful for the preparation for analysis by either TEM or SEM of semiconductors, metals, alloys, ceramics, and other inorganic materials. In one embodiment, a system and process are provided for the preparation of specimens for analysis by transmission electron microscopy including a specimen processing chamber, at least two ion beam generators, and a specimen support or holder. An ion beam masking member is secured to a surface of the specimen and the specimen is milled. Preferably, the system also includes the ability to view the progress of the milling operation and may include an imaging device such as a light microscope which permits monitoring of the area of interest on a specimen as the specimen is milled.

49 Claims, 7 Drawing Sheets

OTHER PUBLICATIONS

Senz et al., Optimisation of the wire–shadow TEM cross-–section preparation technique, Ultramicroscopy 70 (1997) 23–28.

Alani et al., An updated Gas Source Focused Ion Beam Instrument for TEM Specimen Preparation, Mat. Res. Soc. Symp. Proc. vol. 254, 1992 Materials Research Society, pp. 65–78.

Brochure, FB–2000A Focused ION Beam System, Hitachi, pp. 1–5.

Alani et al., An Updated Ion Polishing System for TEM Specimen Preparation of Materials, Mat. Res. Soc. Symp. Proc. vol. 480, 1997 Materials Research Society, pps. 263–292.

Brochure, Model 645 PIMS Precision Ion Milling System, Gatan.

L. Berthold and E. Langer, TEM–Cross Section Preparation Using Wire Shadowing.

Internet document, Ion Milling with RES 100, BAL–TEC.

Brochure, Model 691 Precision Ion Polishing System (PIPS), Gatan.

Internet document, Alani et al., Recent Advances in Broad Ion Beam Techniques: Instrumentation for SEM Specimen Preparation of Semiconductors, Cahners,Semiconductor International.

* cited by examiner

ION BEAM MILLING SYSTEM AND METHOD FOR ELECTRON MICROSCOPY SPECIMEN PREPARATION

CROSS REFERENCE TO RELATED APPLICATION

This application is a continuation of U.S. patent application Ser. No. 09/874,766, filed Jun. 5, 2001 now U.S. patent No. 6,768,110, which claims the benefit of U.S. Provisional Application Ser. No. 60/212,963, filed Jun. 21, 2000.

BACKGROUND OF THE INVENTION

This invention relates to a method and system for the preparation of specimens for analysis by electron microscopy, and more particularly to a method and system for the milling of specimens using an ion beam.

Ion beam milling systems are used for the preparation of specimens whose internal and surface structures are then analyzed using transmission electron microscopy (TEM) or scanning electron microscopy (SEM). Many techniques have been developed which have included the use of mechanical cutting, grinding, and/or polishing operations in combination with ion beam bombardment. In many instances, such techniques have required that the specimen be repeatedly moved from one apparatus to another (either different preparation devices or observation devices) and/or be moved or realigned while mounted in a cutting, grinding, or milling device.

Transmission electron microscopy is an important technique for studying the detailed microstructure of many materials. Improvements in the design and operation of electron microscopes have generated considerable interest in obtaining atomic resolution images of various materials. However, the preparation of specimens for atomic resolution transmission electron microscopy is demanding, requiring a final specimen which is very thin (i.e.,<50 nm) and free from artifacts. Typically, specimen preparation involves initial slicing, sectioning, trepanning, and/or grinding operations to produce a relatively thin (100–200 $\mu$m) disk of approximately 3 mm diameter.

Ion beam milling systems have been used to prepare specimens of various materials including ceramics, semiconductors, metals, and combinations thereof for atomic resolution transmission electron microscopy. In such ion beam milling systems, such as the system disclosed in commonly-assigned U.S. Pat. No. 5,009,743, to Swann, specimens are mounted on holders and placed in the path of one or more ion beams. The ion beams gradually remove atoms from the surface of the specimen until a small perforation is formed in the center of the specimen. Generally, the area immediately around the perforation is then thin enough (i.e.,<50 nm) for atomic resolution analysis by a transmission electron microscope.

Swann et al, U.S. Pat. No. 5,472,566, provides a specimen holder adapted to permit the simultaneous two-sided ion beam milling of a specimen at very low angles of beam incidence, down to 0°, from both sides of the specimen through the use of one or more support arms to secure the specimen. This produces both rapid milling as well as reducing artifacts to provide high quality specimens for transmission electron microscopy analysis.

In such ion beam milling systems, the ion milled specimens have to be removed from the specimen holders and loaded in a TEM holder for imaging. Clearly, loading and unloading of the specimen from the holders increases the potential of damage to fragile specimens. Additionally, if the specimen is not completely electron transparent upon initial TEM examination, it must be returned to the ion mill for further thinning. Multiple milling steps may be required, depending upon thickness requirements at the area of interest in the specimen.

Slope cutting by directing an ion beam at a masking screen located at or near a specimen surface is also known. The masking screen protects a portion of the specimen, while the remainder of the specimen is milled by the ion beam to reveal desired profiles. This technique is capable of providing cross-sectional profiles of layered structures, the surfaces of which can then be studied by scanning electron microscopy. For example, Hauffe, East German published Patent Application No. 201,538, teaches an apparatus and method for preparing specimens for SEM analysis by providing an ion gun inside the specimen chamber of a scanning electron microscope. A mask is positioned adjacent the sample and is used, in conjunction with the ion gun, to remove material from the specimen.

Double slope cutting to produce a very thin film of a specimen for TEM analysis has also been developed. Yoshioka et al, U.S. Pat. No. 5,907,157, describe a method and apparatus for preparing a specimen adapted for electron microscopy which includes an evacuated specimen-processing chamber. A specimen having a surface to be processed is placed inside the processing chamber and a beam-blocking member is placed close to the processed surface so as to block a part of an etching beam. A first etching step is performed by directing the beam at the specimen via the blocking member. Then, the specimen and the blocking member are moved relative to each other to expose another portion of the specimen. A second etching step is then performed by directing the beam at the specimen via the blocking member. As a result, the specimen is thinned and can be observed with an electron microscope. However, the requirement that the specimen and blocking member be moved relative to one another to perform the second etching step complicates the process and introduces the potential for errors as the relative positions of the two must be controlled to within an accuracy on the order of a few hundred nanometers ($10^{-9}$ meters) or less.

Mitro et al, U.S. Pat. No. 5,922,179, teaches an apparatus and process for etching and coating specimens in a single vacuum chamber, to minimize handling and transfer. The apparatus includes a sealed chamber and a vacuum pump for forming and maintaining a vacuum in the chamber, a first ion gun positioned in the chamber to etch a specimen, a sputtering target in the chamber, and at least one additional ion gun positioned in the chamber to cause material from the target to be directed onto the specimen.

Techniques have also been developed in the preparation of specimens for scanning electron microscopy in which the specimen may be observed by a SEM during preparation thereof. For example, Grunewald, U.S. Pat. No. 5,986,264, teaches an ion beam milling system using two ion guns for use in the preparation of samples to be used in both SEM and TEM analysis. The system uses an SEM as a high resolution imaging device to observe the progress of the ion milling of a sample and to determine when a proper sample thickness has been achieved. Also, as the sample stage can be tilted, the system is also taught to be useful for slope cutting of specimens.

The inadequacy in localized thinning of TEM specimens with broad ion beams, coupled with the ability of focused ion beam (FIB) to micro-machine materials, has led to the development of FIB milling systems. The first FIB based instrument (Precision Ion Milling System (PIMS)), became commercially available in 1984 from Gatan, Inc. Since the introduction of this instrument, several other commercial FIB systems have become available. These machines are capable of both imaging and milling selected areas within TEM and SEM specimens with submicron resolutions. The PIMS system is a gas ion source (argon) instrument, whereas the newer generation FIB systems employ liquid metal (gallium) ion sources having superior milling and imaging capabilities.

Specimens are normally milled in gallium based FIB systems with higher energy ions (compared to the PIMS), which may produce a thick amorphous surface artifact (damaged layer). This damaged layer should be removed to produce high quality specimens. Post-FIB milling in broad ion beam systems for final milling and cleaning of such specimens is a common practice. Specifically, FIB milled specimens have been re-milled and cleaned in broad ion beam machines using the specimen holder described in the above-mentioned U.S. Pat. No. 5,472,566 to improve specimen quality. However, again, this requires moving the specimen among various specimen preparation systems and the final TEM or SEM.

Others have reported the use of a wire shadow technique for TEM specimen preparation. Senz et al, *Ultramicroscopy* 70 (1997) pp. 23–28, and Langer, Elektronenoptische Untersuchung des Werkstoffverhaltesn in mechanisch belasteten Mikrobauteilen (1996) teach gluing a wire onto a specimen surface and exposing the surface to ion milling by a Gatan Duo-Mill. The non-shadowed areas of the specimen are removed, and a thin area is produced in the wire shadow.

However, a need still exists in this art for simplified methods and techniques for specimen preparation for both SEM and TEM analysis.

SUMMARY OF THE INVENTION

The present invention provides a method and system for the preparation of specimens for analysis by electron microscopy which utilizes ion beam milling, but without the need for multiple positioning, cutting, and/or handling steps. The system and process are especially useful for the preparation for analysis by either TEM or SEM of semiconductors, metals, alloys, ceramics, and other inorganic materials.

In accordance with one aspect of the present invention, a system and process are provided for the preparation of specimens for analysis by transmission electron microscopy. The system includes a specimen processing chamber, at least two ion beam generators, and a specimen support or holder. Preferably, the system also includes the ability to view the progress of the milling operation and may include an imaging device such as a light microscope which permits monitoring of the area of interest on a specimen as the specimen is milled.

Specimens are prepared by initially forming, cutting, and/or polishing the specimen into a piece having a preferred maximum length of about 3 mm, a width of from about 500–1000 microns, and a thickness of from about 20–150 microns. The edge (thickness dimension and surface of interest for analysis) of the specimen should be relatively flat. A preferred shape for the specimen is a generally semi-circular disc having a radius of about 3 mm and a thickness of from about 20–150 microns, although other shapes may be utilized.

An ion beam masking member is then secured to the edge (thickness dimension and surface of interest for analysis) of the specimen using a suitable adhesive such as an epoxy glue or using a suitable mechanical attachment mechanism. The ion beam masking member is preferably a fiber having a diameter of less than about 100 microns, preferably less than about 80 microns, and most preferably less than about 35 microns and a length which approximates the length of the edge of the specimen. Fibers having diameters down to about 7 microns have been found to be suitable for use. Alternatively, the ion beam masking member may have a non-circular cross-section including square, rectangular, elliptical, or other geometric shape. Preferably, the ion beam masking member comprises an amorphous or single crystal material such as carbon (either amorphous, graphitic, or diamond), silicon carbide, or sapphire. In one embodiment of the invention, the ion beam masking member may be pre-milled prior to securing it to the specimen through ion beam exposure to reduce its diameter or cross-section. This permits a more precise mounting and placement of the masking member on the surface of the specimen relative to features of interest on or in the specimen.

For TEM analysis, once the specimen has been mounted onto a support or holder and installed in the processing chamber, the specimen and ion beam masking member are exposed to two or more ion beams to mill and thin exposed areas on the edge of the specimen. Generally, the surface of interest on the specimen will be positioned perpendicular or nearly perpendicular to the direction of the ion beams. Preferably, an ion beam having a higher intensity in the center of the beam is utilized. That is, for an ion beam having a generally circular cross-section, the intensity at or near the center of the circle is higher than at the edges.

The ion beams will mill both the ion beam masking member as well as the specimen surface causing a necking or thinning of the masking member as milling is continued. Likewise, the masked area of the specimen beneath the ion beam masking member will also be thinned as milling continues because of the thinning of the masking member. The protected area beneath the masking member may be monitored using a suitable imaging device such as an optical or scanning electron microscope which is arranged generally perpendicular to the axis of the ion beams and which provides real time information concerning the progress of the milling process. Alternatively, a light emitting diode and photodetector may be arranged to provide an indication of when the specimen has been sufficiently thinned to become optically transparent.

Once the specimen has been thinned sufficiently to be electron transparent (i.e., less than about 200 nanometers, and preferably less than about 100 nanometers), it is removed from the processing chamber and is ready for TEM analysis. During milling, the specimen and ion beam masking member are positioned in tandem so that there is no relative movement between them. This avoids the need to stop the milling operation and accurately reposition the ion beam masking member prior to the resumption of milling as in some prior art processes.

In an alternative embodiment, the present invention provides a system and process for the preparation of specimens for analysis by a scanning electron microscope. In one form, the system includes a specimen processing chamber, at least one ion beam generator, and a specimen support or holder. Preferably, a second ion beam generator is also included. Generally, a specimen will be prepared so that it has a length of from about 4–8 mm, preferably about 6 mm; a height of from about 6 to about 12 mm, preferably about 8 mm; and a thickness of from about 250–750 microns, preferably about 500 microns.

Preferably, the system also includes the ability to view the progress of the milling operation, in real time, and may include an imaging device such as a light microscope which permits monitoring of the area of interest on a specimen as the specimen is milled. Preferably, the system also includes a sputtering target which may be positioned so that one or both of the ion beam generators can sputter material from the target onto the specimen to coat its surface. Thus, once the specimen is etched and coated, it can be moved to an SEM for analysis.

In a preferred form, the specimen is secured to a rotatable specimen stage for milling. After milling has been completed, the specimen stage is rotated (e.g., 90°) to a position where the surface of the specimen is etched (cleaned). The specimen stage is then rotated back to its original position for sputter coating using one of the ion beam generators and a sputtering target.

In yet another embodiment of the present invention, the present invention provides a system and process for the preparation of specimens for analysis by a scanning electron microscope in a processing chamber which also includes an SEM. The SEM is arranged such that the specimen milling and preparation process is observable with the SEM being utilized as a high resolution imaging device. The ability to observe the milling process in real time permits precise positioning of the specimen and monitoring of the process. Further, the milled specimen can be analyzed directly in the chamber without movement to a separate apparatus.

Accordingly, it is a feature of the present invention to provide a method and system for the preparation of specimens for analysis by electron microscopy which utilizes ion beam milling, but without the need for multiple cutting, positioning, and/or handling steps. It is another feature of the invention to provide a system and process which is adaptable for specimen preparation for both TEM and SEM analysis. These, and other features and advantages of the present invention, will become apparent from the following detailed description, the accompanying drawings, and the appended claims.

BRIEF DESCRIPTION OF THE DRAWINGS

As an aid in the understanding of the invention, reference will now be made to the drawings which illustrate preferred embodiments of the invention and in which like reference numerals represent like elements.

DETAILED DESCRIPTION OF THE PREFERRED EMBODIMENTS

Figure 1A:
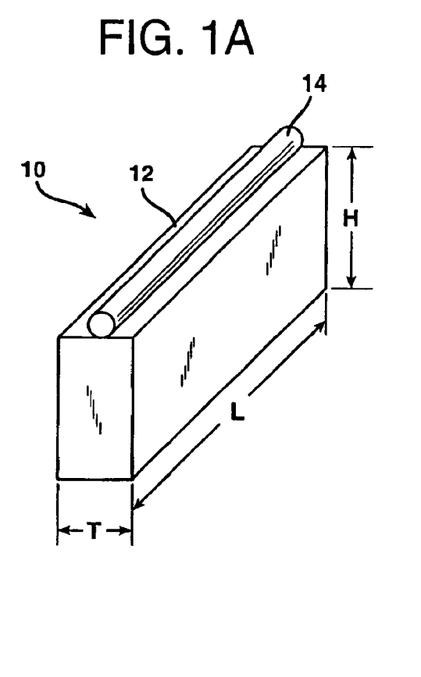
FIGS. 1A, 1B, 1C, and 1D are schematic representations of certain aspects of the ion beam milling system of the present invention illustrating typical specimens and ion beam masking members, with FIGS. 1A–1C depicting specimens mounted for preparation for TEM analysis and FIG. 1D depicting a specimen mounted for preparation for SEM analysis.

With reference to FIGS. 1A–1D, embodiments of the ion beam milling system of the present invention are illustrated to show certain basic elements of the invention. As shown in FIG. 1A, a first specimen 10 having a generally rectangular cross-section with a length, width and height has an edge (surface of interest) 12. Generally, specimen 10 has a maximum length (L) of about 3 mm, a height (H) of from about 500–1000 microns, and a thickness (T) of from about 20–150 microns. The edge (thickness dimension and surface of interest for analysis) of the specimen should be relatively flat.

An ion beam masking member 14 is secured to edge 12 of specimen 10 using a suitable adhesive such as an epoxy glue or a suitable mechanical attachment mechanism. Ion beam masking member 14 is preferably a fiber having a generally circular cross-section and a diameter of from about 7 to less than about 100 microns, preferably less than about 80 microns, and most preferably less than about 35 microns, and a length which approximates the length of edge 12 of the specimen. Alternatively, ion beam masking member 14 may have a non-circular cross-section including square, rectangular, elliptical, or other geometric shape. Preferably, the ion beam masking member comprises an amorphous or single crystal material such as carbon (either amorphous, graphitic, or diamond), silicon carbide, or sapphire. In one embodiment of the invention, ion beam masking member 14 may be pre-milled prior to securing it to specimen 10 through ion beam exposure to reduce its diameter or cross-section. This permits a more precise mounting and placement of the masking member on the surface of the specimen relative to features of interest on or in the specimen.

Figure 1B:
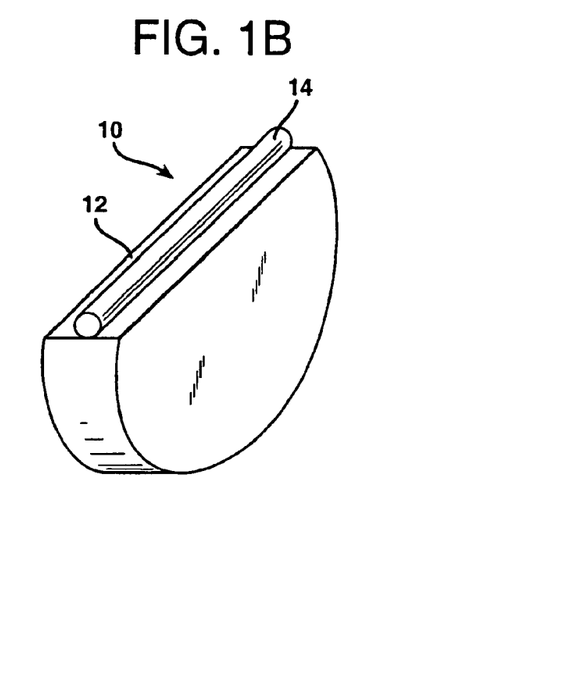
Figure 1C:
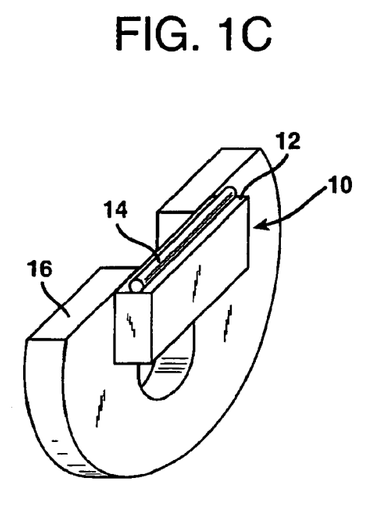

FIG. 1B illustrates another preferred form for specimen 10. As shown in FIG. 1B, specimen 10 is a generally semi-circular disc having a radius of about 3 mm and a thickness of from about 20–150 microns. Shapes other than semicircular may be utilized, although at least one edge or surface of interest should be relatively flat in order to position ion beam masking member 14. FIG. 1C illustrates yet another embodiment of the invention in which specimen 10 is secured (by a suitable adhesive such as an epoxy glue) to a semi-circular disc 16 which has a radius of about 3 mm. Circular 3 mm discs are readily commercially available for use in transmission electron microscopy applications and can be modified to a semicircular shape.

Figure 1D:
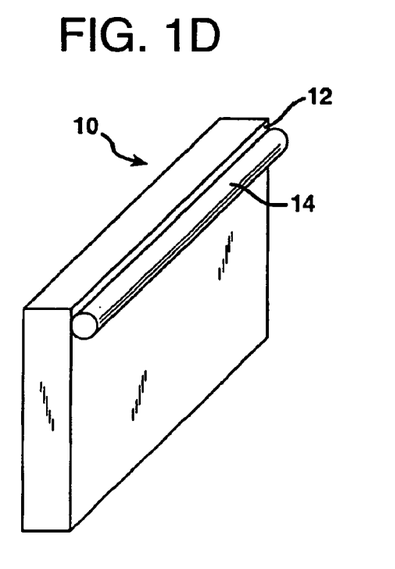

FIG. 1D illustrates an embodiment of the invention adapted for the preparation of specimens for SEM analysis. Specimen 10 may be generally rectangular in cross-section with a length, width, and height. Specimen 10 includes a surface of interest 12 with ion beam masking member 14 mounted adjacent thereto. Typically, specimen 10 may have a length of from about 5–10 mm, a height of from about 3–7 mm, and a thickness of from about 0.25 to 0.75 mm. Edge 12 of the specimen is preferably relatively flat.

FIGS. 2A–2D illustrate the specimens 10 after ion milling. In the embodiments shown in FIGS. 2A–2C, the ion guns (not shown in FIGS. 2A–2C, but shown in FIG. 4B) are positioned substantially perpendicular to the surface 12 of specimen 10. As shown, the ion milling erodes the unprotected areas on surface 12, narrowing the thickness of specimen 10 thereby producing milled areas 22. Also, as ion milling progresses, the diameter of ion masking member 14 is narrowed or necked down as shown, producing a very thin diameter masking area 18 over specimen 10. In certain instances, the milling operation may be continued until masking member 14 is severed leaving two opposing sharp tips.

The preferred ion milling apparatus comprises a rare earth magnet Penning ion discharge gun. Penning guns provide a number of advantages. Penning ion guns provide a high density ion flux and operate over a broad range of ion energies. Penning guns are more powerful than other ion beam generating devices; the generated ion beams can be focused to obtain more rapid milling and sample preparation. Further, Penning guns produce an ion beam which has a higher intensity in the center of the beam. That is, for an ion beam having a generally circular cross-section, the intensity at or near the center of the circle is higher than at the edges. Further, Penning ion guns have low maintenance requirements, with no need for replacement parts. The sputter deposits produced from such ion guns in high quality and amorphous.

Figure 2A:
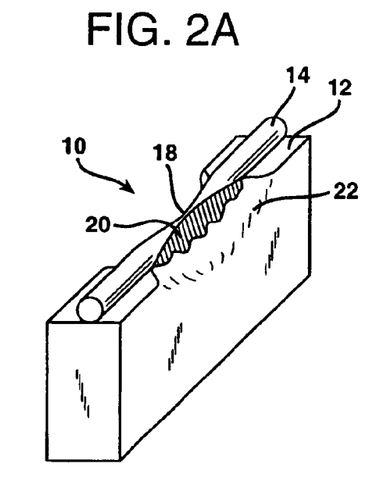
FIGS. 2A, 2B, 2C, and 2D are schematic illustrations of certain preferred embodiments of the invention which illustrate the preparation of typical specimens for analysis, with FIGS. 2A–2C depicting specimens prepared for TEM analysis and FIG. 2D depicting a specimen prepared for SEM analysis.
Figure 2B:
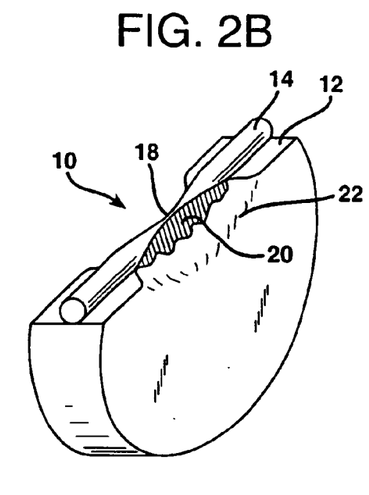
Figure 2C:
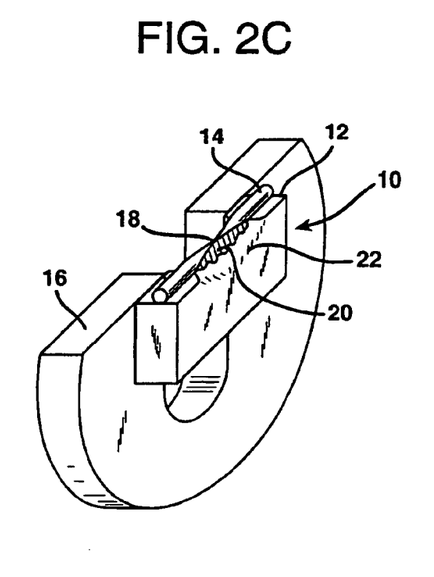

Thus, as milling progresses, area 20, which is located immediately beneath the thinned or necked area 18 of masking member 14, becomes electron transparent. That is, the thickness of area 20 is sufficiently eroded away to produce a thickness of less than about 200 nanometers, and preferably less than about 100 nanometers. The progress of the milling operation may be viewed in real time by positioning an optical detector or other imaging device to focus on area 20 as will be explained in greater detail below.

Figure 2D:
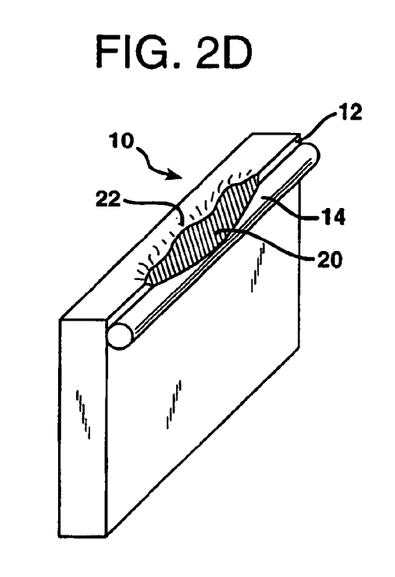

In the embodiment shown in FIG. 2D, milling takes place along masking member 14 to expose an area of interest 20. Typically, for SEM analysis, an angled cut is made to expose successive layers through the thickness of the specimen. The area 20 may then be etched (cleaned) and coated for SEM analysis.

Figure 3:
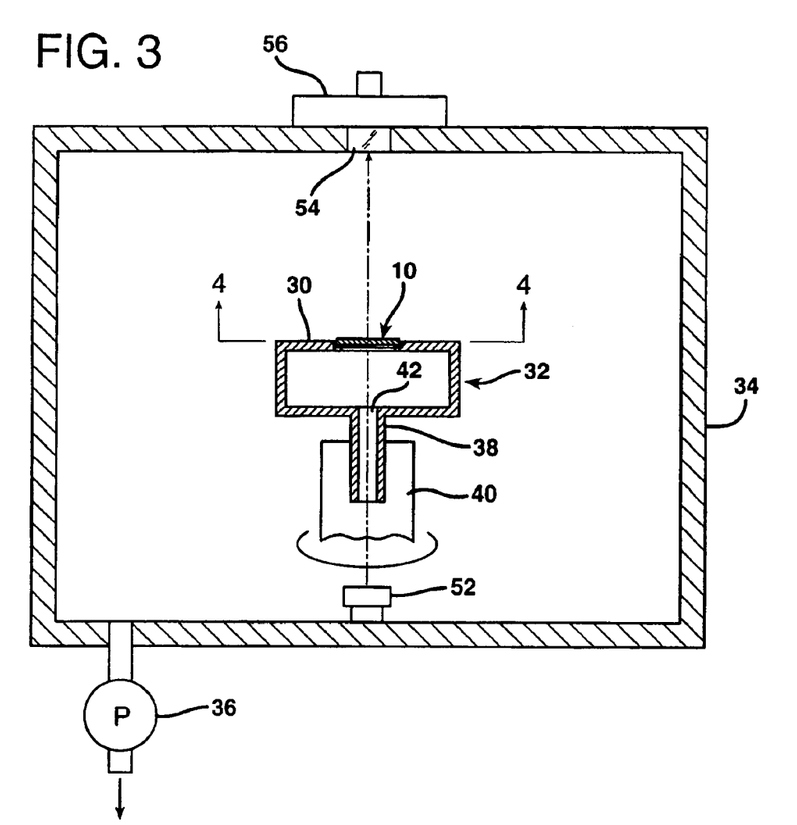
FIG. 3 is a schematic cross-sectional view of an ion beam milling system in accordance with an embodiment of the present invention.
Figure 4A:
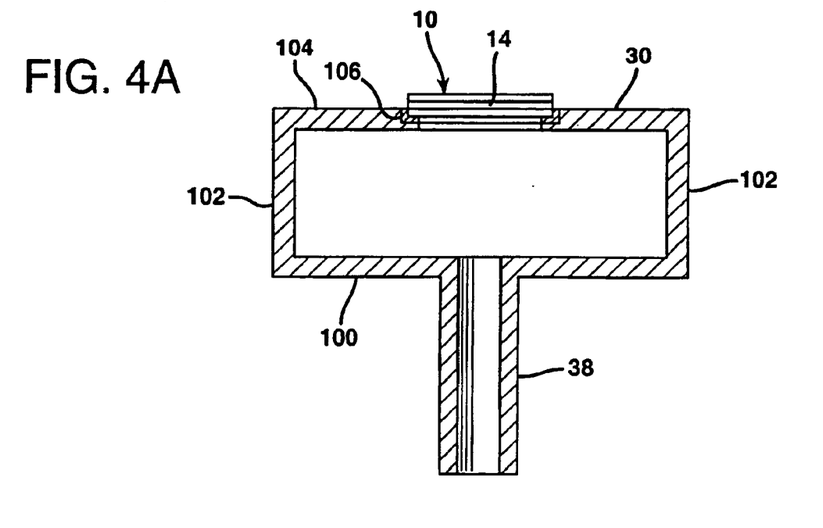
FIG. 4A is an enlarged cross-sectional view of the specimen holder and specimen in the ion milling chamber.
Figure 4B:
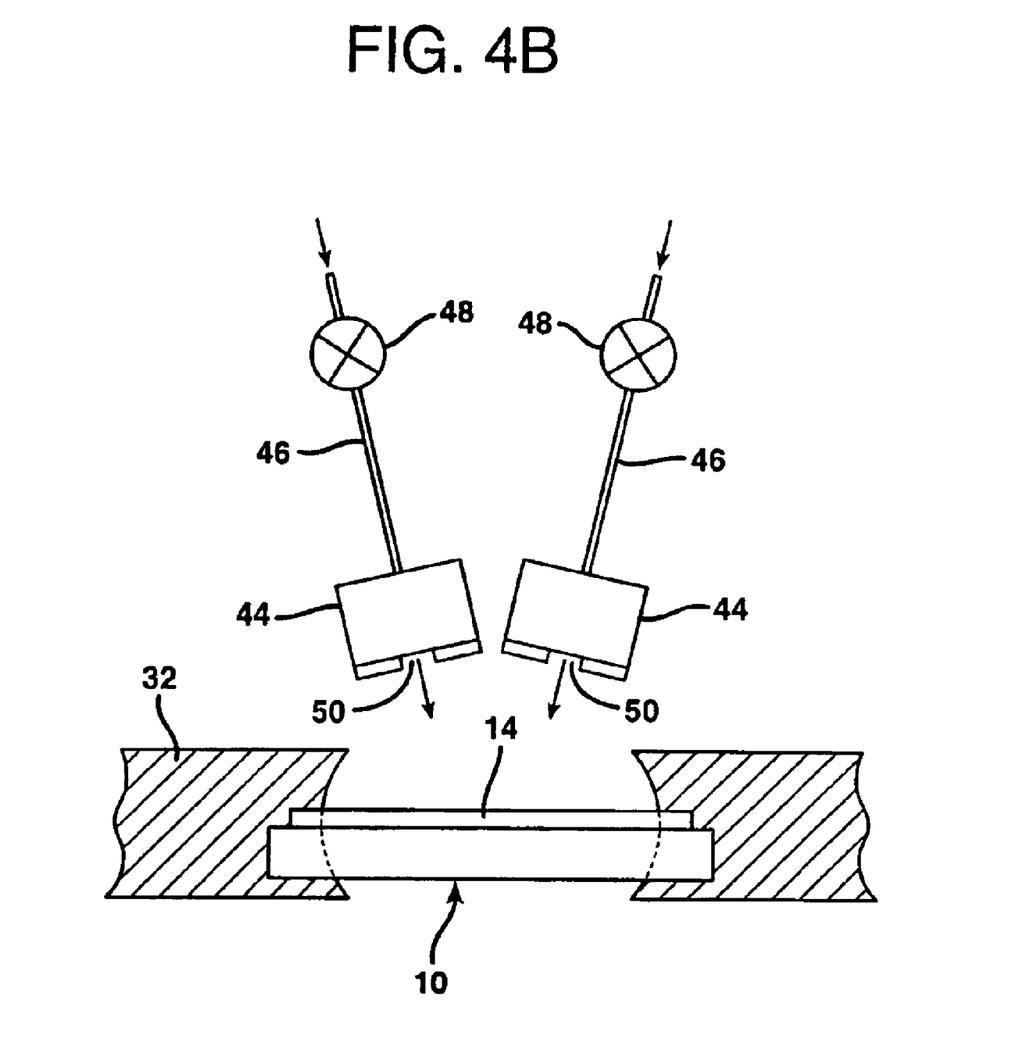
FIG. 4B is a schematic view taken along line 4—4 in FIG. 3.

Referring now to FIGS. 3 and 4, schematic cross-sectional and top views of one embodiment of an ion beam milling system in accordance with the present invention are shown. The system is a modification of the system described in commonly-assigned Swann et al, U.S. Pat. No. 5,472,566, the disclosure of which is hereby incorporated by reference. As shown, specimen 10 is supported by support arms 30 of a specimen holder in vacuum chamber 34. Suitable means, such as a high vacuum pump 36 capable of reducing the pressure in chamber 34 to about $10^{-6}$ Torr, are used to evacuate the chamber. A preferred vacuum system is described in Mitro et al, U.S. Pat. No. 5,922,179 and includes a drag pump manifold connected to a molecular drag pump and a backing molecular drag pump with an oil-free diaphragm pump. The use of an oil-free system is preferred to eliminate the possibility of introducing any hydrocarbon contamination from the lubricating oils in the pumps into vacuum chamber 34.

The pedestal 38 of the specimen holder is fitted onto a holder mount 40. Holder mount 40 may be rotated, by suitable rotary drive means (not shown), to cause specimen 10 to rotate during ion milling. Support arms 30 position specimen 10 so that it is generally centered over bore 42.

As shown in FIG. 4A, preferably each support arm 30 includes a first portion or segment 100 which extends generally laterally away from pedestal 38, a second upstanding portion or segment 102, and a third portion or segment 104 which extends generally laterally back toward the center axis of pedestal 38. In this manner, support arm 30 holds specimen 10 and ion beam masking member 14 in a predetermined spaced distance away from pedestal 38 but generally centered over bore 20. Of course it will be apparent to those skilled in this art that the particular configuration is not crucial and that other support structures may be utilized. What is important is that the support arm is designed to position the specimen a spaced distance away from the pedestal to provide for line-of-sight clearance for the ion gun arrangement and to permit the ion beam or beams (containing energized neutrals and ions) to impinge upon specimen 10 and ion beam masking member 14.

An adhesive-type specimen holder is depicted as an example of one type of holder which may be used in the practice of the present invention. Small recesses 106 are provided adjacent the tips of support arms 30 in segment 104. The recesses are of a depth slightly less than the typical thickness of a specimen 10 (e.g., 100–200 μm), or a specimen holder upon which the specimen is mounted. Further, the recesses have a diameter slightly greater than the diameter of the specimen (or holder) so that the specimen will seat in those recesses. Other specimen holders may also be utilized including those where ion beam masking member 14 is mechanically attached or secured to specimen 10. Examples of suitable mechanical attachment mechanisms such as clamps and springs are shown in commonly-assigned Swann et al, U.S. Pat. No. 5,472,566.

A pair of ion guns 44 (shown in FIG. 4B) of substantially identical construction are connected to power supplies (not shown). Desirably, the ion guns are independently adjustable and positionable within the vacuum chamber. Preferably, the ion guns are Penning ion discharge guns. In the configuration illustrated in FIG. 4B (where angles are exaggerated for simplification), both ion guns are positioned adjacent specimen 10 to direct respective ion beams against the upper and lower surfaces of ion beam masking member 14. Typically, both ion guns will be positioned substantially perpendicularly to the edge of interest on specimen 10 to be milled. Thus, for this configuration, the ion guns are positioned to discharge their ions along a generally horizontal plane, typically at low angles of from about 1–10° from the horizontal plane, with one ion gun positioned slightly above the horizontal plane and one ion gun positioned slightly below that plane. A gas, typically argon, is supplied to the ion guns through gas supply line 46, the supply of gas being regulated by valve 48. Ion guns 44 produce beams of energetic particles which impinge onto ion beam masking member 14 and the unprotected surfaces of specimen 10 through their respective front apertures 50.

A light source 52 (shown in FIG. 3), such as, for example a light emitting diode (LED), projects light generally vertically through pedestal bore 42. Milling may be terminated when the surface of specimen 10 in area 20 (FIG. 2A) is perforated or just prior to perforation when the surface of specimen 10 is sufficiently transparent so that the light from source 52 passes through specimen 10 and window 54 and impinges on a photodetector 56. Photodetector 56 may be connected through suitable circuitry (not shown) to terminate the power to ion guns 44 when it detects a predetermined threshold of light. Alternatively, a light microscope or other imaging device may be used to monitor the progress of milling and to terminate operation of the ion guns when a suitable electron transparent thickness is achieved.

Sector ion milling may be carried out by controlling power to the ion guns 44 using a suitable controller (not shown) such that power is supplied whenever the specimen holder 32 is rotated to a position where there is line-of-sight clearance to the surface of specimen 10 and power is terminated whenever, due to rotation, support arms 30 enter the path of the ion beams. This reduces specimen contamination from sputtering of metal from either the support arms or the pedestal. Sector ion milling also provides uniform milling of multilayer materials and high quality specimens for analysis.

Thus, the present invention provides for the preparation of specimens for TEM analysis by first preparing a small specimen with the aid of an imaging device such as a light microscope or a scanning electron microscope and mounting the ion beam masking member onto the suitably prepared specimen. The specimen and ion beam masking member are then subjected to broad ion beam milling while monitoring the progress of the milling operation. Once the milling has achieved an electron transparent region on the specimen, the specimen is ready for TEM analysis. Alternatively, after broad ion beam milling has sufficiently thinned the specimen, the specimen may be transferred to a focused ion beam (FIB) apparatus where precision milling is continued on the region of interest. Such focused ion beam apparatuses are commercially available. Moreover, specimens prepared for TEM analysis also are potentially useful in SEM analysis.

The present invention is also useful in the preparation of specimens for analysis by a scanning electron microscope (SEM). Again, the specimen is prepared and the ion beam masking member is secured to the specimen using suitable adhesives or mechanical attachments devices. A broad ion beam milling system is then used to cut and etch the sample to expose a surface of interest. In one embodiment, the specimen may be mounted onto a rotatable stage for the milling/cutting operation. The stage may then be rotated (e.g., 90°) for etching of the surface which has been exposed. Tiltable and/or rotatable specimen stages are commercially available.

To aid in SEM analysis, the specimen may then be coated with a suitable material such as a noble metal or other conductive material. In one embodiment, this is accomplished by providing a rotatable specimen stage and a movable metal sputtering target. Once the exposed surface of the specimen has been etched, the specimen stage is rotated back to its initial position, the sputtering target is uncovered or moved, and the ion beam generator is repositioned to sputter metal from the target onto the exposed specimen surface to coat it. A suitable apparatus for precision etching and coating of specimens is described in commonly-assigned Mitro et al, U.S. Pat. No. 5,922,179, the disclosure of which is hereby incorporated by reference.

Figure 5:
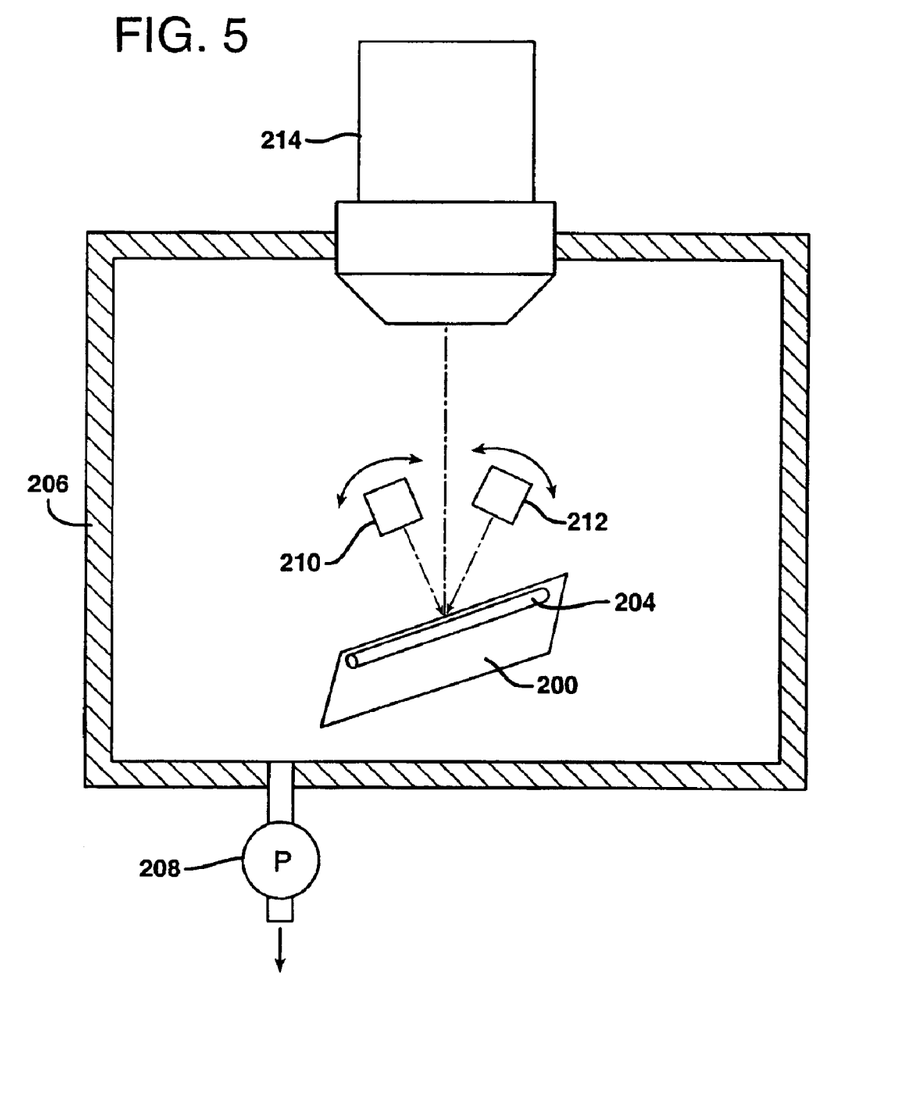
FIG. 5 is a schematic cross-sectional view of an ion beam milling system in accordance with another embodiment of the present invention.

In another embodiment of the invention as illustrated in FIG. 5, an ion milling system is schematically shown and includes one or more ion guns which mill the specimen in conjunction with a scanning electron microscope which is utilized first as a high resolution imaging source to monitor the progress of the milling and next as an analysis tool for the milled specimen. As shown, specimen 200 has an ion beam masking member 204 secured to an edge thereof. As is conventional, the specimen is supported on a holder (not shown) which is capable of tilting the specimen about a longitudinal axis. The specimen is positioned in a vacuum processing chamber 206 with a source of vacuum such as vacuum pump 208.

In the embodiment shown in FIG. 5, there are two ion guns 210 and 212 which are designed to discharge energetic ions (such as, for example, argon) to mill specimen 200 in the area immediately adjacent ion beam masking member 204. Where the FIG. 5 embodiment is used for SEM analysis, only one of the ion guns need be used, and the ion beam is aimed along one side of ion beam masking member 204. An imaging device such as a light microscope or scanning electron microscope 214 is positioned to monitor the progress of milling and to analyze the milled sample once the profile of interest has been exposed. Again, as described above, the chamber may also optionally include a sputtering target of, for example, a noble metal. One of both of the ion guns may be aimed to cause material to be sputtered off of the target and onto specimen 200. In a typical arrangement, the specimen will be coated with a thin amorphous layer of a conductive material. For example, the sputtering target may comprise chromium, platinum, gold-platinum, iridium, tungsten, or carbon. The thickness of the coating may be monitored and measured using conventional techniques. Generally, the target may be sputter cleaned prior to deposition of the coating for a short initial period by exposing it to the energized stream of ions and neutrals.

Figure 6:
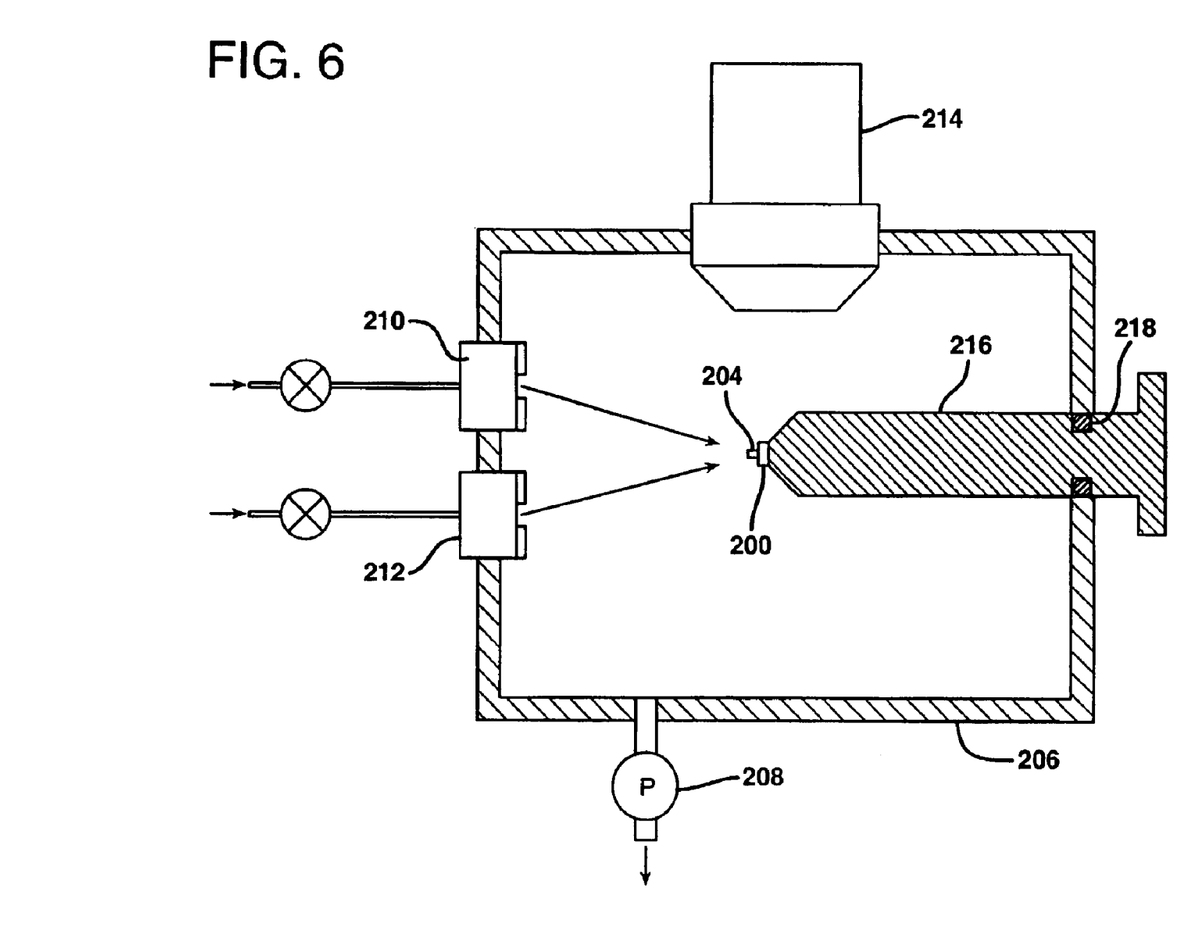
FIG. 6 is a schematic cross-sectional view of an ion beam milling system in accordance with yet another embodiment of the present invention.

FIG. 6 (where like elements are represented by like reference numerals) illustrates yet another embodiment of the invention for TEM specimen preparation which provides the advantage that both sides of the specimen may be milled as well as monitored during preparation. Again, two ion guns 210 and 212 are aimed such that they emit energetic ions toward specimen 200 and ion beam masking member 204 to mill specimen 200 on both sides of masking member 204. An imaging device such as a light microscope or a scanning electron microscope 214 is positioned to monitor the progress of milling and to provide analysis of the milled sample once the area of interest has been exposed. As shown, specimen 200 is mounted onto a rotatable, generally horizontally oriented mechanism 216 which permits the specimen to be turned (rotated) such that the areas on both sides of the masking member 204 may be milled, monitored, and imaged (analyzed). In a preferred form, mechanism 216 is an airlock whose position may be mechanically and/or hydraulically controlled to insert and remove the specimen 200 from the chamber 206. An O-ring 218 or other suitable seal preserves the vacuum in the chamber.

Figure 7:
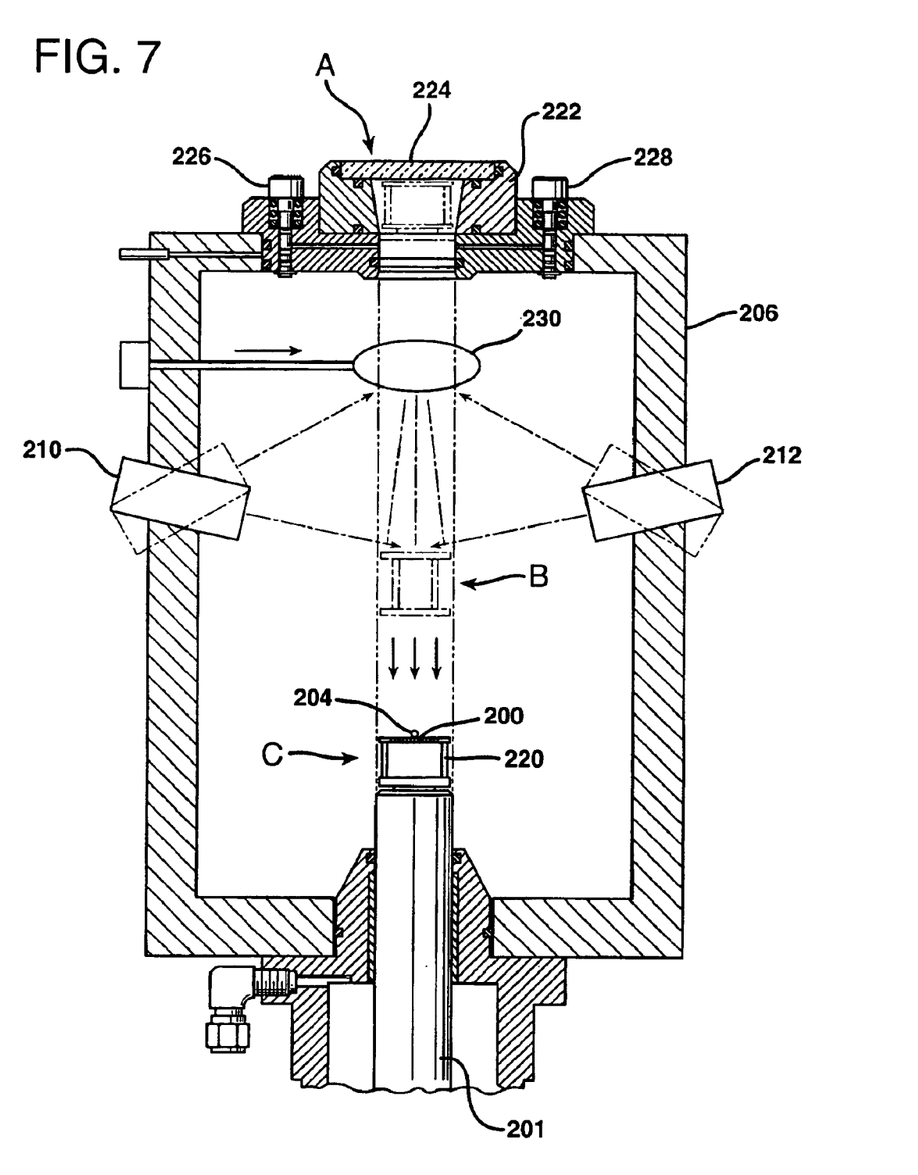
FIG. 7 is a schematic side view of an ion beam milling system in accordance with yet another embodiment of the present invention including a mechanism capable of moving the mounted specimen into position for specimen exchange, milling and etching, and surface coating.

FIG. 7 illustrates still another embodiment of the invention designed for the preparation of specimens for SEM analysis. In this embodiment, a three-stage elevator 201 is oriented for vertical movement of specimen 200. A suitable device for moving the specimen is shown in commonly-assigned Swann, U.S. Pat. No. 4,272,682, the disclosure of which is incorporated by reference. At a first position or stage, generally indicated by dashed lines at A, the specimen 200 can be mounted onto a specimen stage or holder 220 in an airlock 222 outside of the vacuum chamber 206. Other specimens of interest can be exchanged for preparation and/or analysis at this location. Also, the specimen may be closely observed through transparent viewing window 224. Airlock 222 is operated by alternately depressing vacuum valves 226 and 228 either to admit air into or evacuate air out of the airlock.

At a second position or stage indicated by dashed lines at B, the specimen is lowered into vacuum chamber 206. Ion guns 210 and 212 are aimed such that specimen 200 is milled at an appropriate area of interest. As described above, depending on the desired use of the specimen, it may be thinned on both sides of masking member 204 for TEM analysis, or may be milled on one side to expose a surface of interest for SEM analysis.

At a third position or stage indicated at C, the specimen 200 is further lowered into vacuum chamber 206, and ion guns 210 and 212 are rotated to positions shown by the dashed lines. A sputtering target 230 is moved from a protected position in the direction of the arrow to a position where the ions from guns 210 and 212 impinge upon it. Material (such as metal) from target 230 is then sputtered onto the surface of specimen 200 to coat the specimen in preparation for analysis. The coated specimen may be removed from chamber 206 by raising elevator 201 to position the specimen within airlock 222. Sputtering target 230 is illustrated for convenience as emerging from a location in the same plane as ion guns 210 and 212. However, it is apparent that target 230 may be positioned at any point about the perimeter of chamber 206.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. An ion beam milling system for electron microscopy specimen preparation comprising: a chamber communicating with a source of vacuum for said chamber, a specimen holder, a specimen having length and thickness dimensions, said specimen mounted to said specimen holder, and an ion beam masking member secured to a surface comprising the thickness dimension of said specimen such that there is no relative movement between said specimen and said ion beam masking member during milling, and at least one ion gun positioned to cause milling of said surface of said specimen to provide an electron transparent surface of said specimen adjacent said ion beam masking member.

2. An ion beam milling system as claimed in claim 1 in which said ion beam masking member on said surface of said specimen is positioned substantially perpendicular to streams of energized ions and neutrals emitted from said at least one ion generating gun.

3. An ion beam milling system as claimed in claim 1 in which said ion beam masking member is thinned during said milling.

4. An ion beam milling system for electron microscopy specimen preparation comprising: a chamber communicating with a source of vacuum for said chamber, a specimen holder, a specimen having length and thickness dimensions, said specimen mounted to said specimen holder, and an ion beam masking member comprising a fiber having a length substantially equal to the length of said specimen secured to a surface comprising the thickness dimension of said specimen such that there is no relative movement between said specimen and said ion beam masking member during milling, and at least one ion gun positioned to cause milling of said surface of said specimen to provide an electron transparent surface of said specimen adjacent said ion beam masking member.

5. An ion beam milling system as claimed in claim 4 in which said ion beam masking member comprises a material selected from the group consisting of amorphous carbon, graphitic carbon, diamond, silicon carbide, and sapphire.

6. An ion beam milling system as claimed in claim 4 in which said ion beam masking member has a cross section selected from the group consisting of circular, square, rectangular, and elliptical.

7. An ion beam milling system as claimed in claim 4 in which said ion beam masking member has a diameter of from between about 7 to about 100 microns.

8. An ion beam milling system as claimed in claim 7 in which the diameter of said ion beam masking member is pre-milled prior to being secured to said surface of said specimen.

9. An ion beam milling system as claimed in claim 1 including an imaging device adapted for viewing the progress of milling.

10. An ion beam milling system as claimed in claim 9 in which said imaging device comprises a light microscope.

11. An ion beam milling system as claimed in claim 9 in which said imaging device comprises a scanning electron microscope.

12. An ion beam milling system as claimed in claim 1 including a detector adapted to measure the progress of milling.

13. An ion beam milling system as claimed in claim 1 in which said specimen holder is rotatable during milling of said specimen.

14. An ion beam milling system as claimed in claim 13 including a controller for controlling the power supplied to said at least one ion generating gun.

15. An ion beam milling system as claimed in claim 14 in which power to said at least one ion generating gun is controlled to produce sector ion milling of said specimen.

16. An ion beam milling system as claimed in claim 13 in which said specimen holder is rotatable about a generally vertical axis during milling.

17. An ion beam milling system as claimed in claim 13 in which said specimen holder is rotatable about a generally horizontal axis during milling.

18. An ion beam milling system for electron microscopy specimen preparation comprising: a chamber communicating with a source of vacuum for said chamber, a specimen holder, a specimen having height, length, and thickness dimensions mounted on said specimen holder, and an ion beam masking member secured to a surface comprising the length dimension of said specimen adjacent an edge thereof such that there is no relative movement between said specimen and said ion beam masking member during milling, and at least one ion gun positioned to cause milling of said surface of said specimen to expose an area of interest on said specimen adjacent said ion beam masking member.

19. An ion beam milling system as claimed in claim 18 in which said ion beam masking member on said surface of said specimen is positioned such that streams of energized ions and neutrals emitted from said ion generating gun impinge on said sample to mill said specimen along an edge thereof.

20. An ion beam milling system as claimed in claim 18 in which said ion beam masking member is thinned during said milling.

21. An ion beam milling system for electron microscopy specimen preparation comprising: a chamber communicating with a source of vacuum for said chamber, a specimen holder, a specimen having height, length, and thickness dimensions mounted on said specimen holder, and an ion beam masking member a fiber having a length substantially equal to the length of said specimen secured to a surface comprising the length dimension of said specimen adjacent an edge thereof such that there is no relative movement between said specimen and said ion beam masking member during milling, and at least one ion gun positioned to cause milling of said surface of said specimen to expose an area of interest on said specimen adjacent said ion beam masking member.

22. An ion beam milling system as claimed in claim 21 in which said ion beam masking member comprises a material selected from the group consisting of amorphous carbon, graphitic carbon, diamond, silicon carbide, and sapphire.

23. An ion beam milling system as claimed in claim 21 in which said ion beam masking member has a cross section selected from the group consisting of circular, square, rectangular, and elliptical.

24. An ion beam milling system as claimed in claim 21 in which said ion beam masking member has a diameter of from between about 7 to about 100 microns.

25. An ion beam milling system as claimed in claim 24 in which the diameter of said ion beam masking member is pre-milled prior to being secured to said surface of said specimen.

26. An ion beam milling system as claimed in claim 18 including an imaging device adapted for viewing the progress of milling.

27. An ion beam milling system as claimed in claim 26 in which said imaging device comprises a light microscope.

28. An ion beam milling system as claimed in claim 26 in which said imaging device comprises a scanning electron microscope.

29. An ion beam milling system as claimed in claim 18 in which said specimen holder is rotatable.

30. An ion beam milling system as claimed in 18 including a controller for controlling the power supplied to said ion generating guns gun.

31. An ion beam milling system as claimed in claim 30 in which power to said ion generating gun is controlled to produce sector ion milling of said specimen.

32. An ion beam milling system as claimed in claim 29 in which said specimen holder is rotatable about a generally vertical axis during milling.

33. An ion beam milling system as claimed in claim 18 including a sputtering target positioned in said chamber.

34. An ion beam milling system as claimed in claim 33 in which said ion generating gun is movable from a first position to emit an ion beam towards said specimen to a second position to emit an ion beam towards said sputtering target.

35. An ion beam milling system as claimed in claim 18 including an elevator for moving said specimen and specimen holder from a first specimen exchange position to a second milling position to a third coating position.

36. An ion beam milling system for electron microscopy specimen preparation comprising: a chamber communicating with a source of vacuum for said chamber, a specimen holder, a specimen having length and thickness dimensions, said specimen mounted to said specimen holder, and an ion beam masking member secured with an adhesive to a surface comprising the thickness dimension of said specimen such that there is no relative movement between said specimen and said ion beam masking member during milling, and at least one ion gun positioned to cause milling of said surface of said specimen to provide an electron transparent surface of said specimen adjacent said ion beam masking member.

37. An ion beam milling system for electron microscopy specimen preparation comprising: a chamber communicating with a source of vacuum for said chamber, a specimen holder, a specimen having length and thickness dimensions, said specimen mounted to said specimen holder, and an ion beam masking member mechanically attached to a surface comprising the thickness dimension of said specimen such that there is no relative movement between said specimen and said ion beam masking member during milling, and at least one ion gun positioned to cause milling of said surface of said specimen to provide an electron transparent surface of said specimen adjacent said ion beam masking member.

38. An ion beam milling system for electron microscopy specimen preparation comprising: a chamber communicating with a source of vacuum for said chamber, a specimen holder, a specimen having height, length, and thickness dimensions mounted on said specimen holder, and an ion beam masking member secured with an adhesive to a surface comprising the length dimension of said specimen adjacent an edge thereof such that there is no relative movement between said specimen and said ion beam masking member during milling, and at least one ion gun positioned to cause milling of said surface of said specimen to expose an area of interest on said specimen adjacent said ion beam masking member.

39. An ion beam milling system for electron microscopy specimen preparation comprising: a chamber communicating with a source of vacuum for said chamber, a specimen holder, a specimen having height, length, and thickness dimensions mounted on said specimen holder, and an ion beam masking member mechanically attached to a surface comprising the length dimension of said specimen adjacent an edge thereof such that there is no relative movement between said specimen and said ion beam masking member during milling, and at least one ion gun positioned to cause milling of said surface of said specimen to expose an area of interest on said specimen adjacent said ion beam masking member.

40. In combination an electron microscopy specimen having length and thickness dimensions, and an ion beam masking member secured to a surface comprising the thickness dimension of said specimen such that there is no relative movement between said specimen and said ion beam masking member during milling of said specimen to provide an electron transparent surface of said specimen adjacent said ion beam masking member.

41. The combination of claim 40 in which said ion beam masking member comprises a fiber that is secured to said specimen by an adhesive.

42. The combination of claim 40 in which said adhesive comprises an epoxy glue.

43. The combination of claim 40 in which said ion beam masking member comprises a fiber that is mechanically attached to said specimen.

44. The combination of claim 40 in which said ion beam masking member comprises a material selected from the group consisting of amorphous carbon, graphitic carbon, diamond, silicon carbide, and sapphire.

45. The combination of claim 40 in which said ion beam masking member has a cross section selected from the group consisting of circular, square, rectangular, and elliptical.

46. The combination of claim 40 in which said ion beam masking member has a diameter of from between about 7 to about 100 microns.

47. The combination of claim 46 in which the diameter of said ion beam masking member is pre-milled prior to being secured to said surface of said specimen.

48. The combination of claim 40 in which said ion beam masking member is aligned along the length of said specimen.

49. The combination of claim 48 in which said ion beam masking member is substantially centered with respect to the thickness dimension of said specimen.

* * * * *